United States Patent [19]

Dieterich et al.

[11] 3,959,329

[45] May 25, 1976

[54] POLYISOCYANATES CONTAINING SULPHONIC ACID OR SULPHONATE GROUPS

[75] Inventors: Dieter Dieterich, Leverkusen; Peter Markusch; Werner Dietrich, both of Cologne, all of Germany

[73] Assignee: Bayer Aktiengesellschaft, Leverkusen, Germany

[22] Filed: Nov. 29, 1974

[21] Appl. No.: 528,319

Related U.S. Application Data

[63] Continuation-in-part of Ser. No. 363,436, May 24, 1973, abandoned.

[30] Foreign Application Priority Data

Nov. 30, 1973 Germany.............................. 2359615

[52] U.S. Cl.................... 260/453 AR; 260/2.5 AT; 260/75 NT; 260/77.5 AT; 260/471 C
[51] Int. Cl.²...................................... C07C 119/048

[58] Field of Search.. 260/453 AR, 456 P, 77.5 AT, 260/471 C

[56] References Cited
UNITED STATES PATENTS 3,826,769  7/1974  Carlson........................... 260/775 X

*Primary Examiner*—Lewis Gotts
*Assistant Examiner*—Dolph H. Torrence
*Attorney, Agent, or Firm*—Joseph C. Gil; Gene Harsh

[57] ABSTRACT

Liquid and substantially non-crystalline aromatic polyisocyanate sulphonic acids or sulphonates and a process for the preparation thereof are disclosed which polyisocyanates are eminently suitable as presursors in the production of polyurethane foam resins and/or emulsifiers or wetting agents, hydraulic binders, thickening agents and cross-linking agents for vinyl polymers, polyurethanes, polyureas and polyamides.

4 Claims, No Drawings

POLYISOCYANATES CONTAINING SULPHONIC ACID OR SULPHONATE GROUPS

This application relates generally to organic polyisocyanates and more particularly to organic polyisocyanates containing sulphonic acid or sulphonate groups. This application is a continuation-in-part of our application Ser. No. 363,436 filed May 24, 1973 and abandoned.

Diisocyanates which contain sulphonic acid groups are known and are described for example, in German Offenlegungsschrift No. 1,939,911. By reacting tolylene diisocyanate with sulphur trioxide, a crystalline, high melting product is obtained which dissolves in sodium hydroxide solution and undergoes vigorous reaction with water. Such sulphonic acid group containing diisocyanates may be used, for example, in preparing anionic polyurethane dispersions. A disadvantage of the known diisocyanate sulphonic acids is their solid aggregate state combined with their high melting point and insolubility in most conventional solvents. These products can therefore, be used in the preparation of polyurethanes only if it is possible to prepare a homogeneous reaction mixture, for example, by using polar solvents.

For producing polyurethane foams, for example, the known isocyanate sulphonic acids cannot be used, for the reasons mentioned above. Other methods therefore have to be employed for the direct production of solid polyurethane ionomers, for example, the introdouction of tertiary nitrogen functions by way of polyols with a suitable structure followed by alkylation to a quaternary ammonium salt. As is also known from German Offenlegungsschrift No. 1,939,911, that higher molecular weight reaction products of polyether or polyester polyols and polyisocyanates, so-called prepolymers which generally have an isocyanate content of between 2 and 6% may be modified with sulphonic acid groups using sulphuric acid or oleum. The products obtained are generally liquid and in some cases highly viscous and can be worked up for special purposes by the usual methods but their possibilities of application are limited due to their generally high viscosity and particularly to their low NCO content.

It is therefore an object of this invention to provide hitherto unkown polyisocyanates that contain sulphonic acid or sulphonate groups. It is another object of this invention to provide liquid and substantially non-crystalline solid aromatic polyisocyanate sulphonic acids and sulphonates. A further object of this invention is to provide liquid and substantially non-crystalline solid aromatic polyisocyanate sulphonic acids or sulphonates which have a high isocyanate content. An additional object of this invention is to provide liquid aromatic polyisocyanate sulphonic acids and sulphonates which are storage stable and free from sedimentation. Another object of this invention is to provide liquid aromatic polyisocyanate sulphonic acids or sulphonates suitable for use in the production of polyurethane foams. A still further object of this invention is to provide polyurethane foams wherein the polyisocyanate precursors are polyisocyanate sulphonic acids or sulphonates.

The foregoing objects and others which will become apparent from the following description are accomplished in accordance with the invention, generally speaking, by providing liquid and substantially non-crystalline solid aromatic polyisocyanate sulphonic acids or sulphonates prepared by a process comprising sulphonating liquid multicomponent mixtures of aromatic polyisocyanates. Liquid aromatic polyisocyanate sulphonic acids or sulphonates are prepared when the aromatic polyisocyanates in the multicomponent mixture have an NCO content of from about 10% to about 42% and a viscosity of from about 50 to about 10,000 cP and the quantity of sulphonating agent (calculated in terms of sulphur trioxide) used corresponds to from about 0.1% to about 10% by weight of the quantity of polyisocyanate. Brittle solid substantially non-crystalline resinous polyisocyanates are obtained when the viscosity of the multicomponent mixture has a viscosity which is higher than 50 cP at 25°C and the quantity of sulphonating agent calculated as sulphur trioxide is more than 6% and preferably more than 0.1%. The sulphonating reaction may, if desired, be followed by neutralization of the sulphonic acid groups introduced. The liquid products obtained in this way are liquid aromatic polyisocyanate sulphonic acids or sulphonates with a high isocyanate content which are stable in storage and free from sedimentation.

More specifically liquid aromatic polyisocyanates which contain sulphonic acid and/or sulphonate groups are prepared by a process wherein liquid multicomponent mixtures of aromatic polyisocyanates which have an NCO content of from about 10% to about 42% by weight and a viscosity of from about 50 to about 10,000 cP at 25°C are reacted with from about 0.1% to about 10% by weight of sulphur trioxide or an equivalent quantity of oleum, sulphuric acid or chlorosulphonic acid at from about −20° to about 200°C, and the sulphonation products obtained in this manner may be completely or partly neutralized with a basic compound.

It has been found that brittle solid resinous isocyanates are obtained when the viscosity of the isocyanate mixture used as the starting material is higher than 50 cP at 25°C and the quantity of sulphur trioxide used for sulphonation is more than 6% and preferably more than 10.1%. Furthermore, it has been found that the functionality of the isocyanate influences the aggregate state of the sulphonation product. Whereas isocyanates with a functionality of 2.0 to 2.2 generally give rise to liquid isocyanate sulphonic acids, isocyanates which have an average functionality of more than 2.2 very rapidly give rise to high viscous and finally solid, resinous products.

Liquid multicomponent mixtures of aromatic polyisocyanates suitable for preparing liquid aromatic polyisocyanates according to the invention are in particular those which have an NCO content of from about 10% to about 42% by weight, preferably from about 18 to about 35% by weight, and a viscosity of from about 50 to about 10,000 cP, preferably from about 100 to about 5000 cP, at 25°C. It is preferred to use liquid aromatic polyisocyanate mixtures which have an isocyanate-content of about 6 to about 42% by weight, preferably about 18 to about 35% by weight and a viscosity at 25°C of 50 cP to 100,000 cP and an average isocyanate functionality of more than 2.2 for making solid aromatic polyisocyanates which contain sulphonic acid and/or sulphonate groups.

Suitable liquid aromatic polyisocyanate mixtures for preparing either liquid or solid products according to the invention are:

1. The phosgenation products of aniline/formaldehyde condensates which contain 20 to 80% by weight of dinuclear diisocyanates 8 to 70% by weight of trinuclear triisocyanates, 1 to 20% by weight of tetranuclear tetraisocyanates and 1% to 40% by weight of higher nuclear polyisocyanates. Polyisocyanate mixtures of this kind generally have a viscosity of above 50 cP at 25°C.

2. For preparing solid products, liquid aromatic polyisocyanate mixtures within a viscosity range of 10,000 to 100,000 cP at 25°C which represent substantially mixtures of higher homologs or analogs of the polyisocyanates of (1) e.g., phosgenation products of aniline formaldehyde condensates containing at least 50% by weight of trifunctional and higher functional polyisocyanates, solutions in such phosgenation products of distillation residues obtained from the distillation of commercial tolylene diisocyanate mixtures, which solutions contain up to 60% by weight of distillation residue. Distillation residues of this kind and the corresponding solutions have been described, for example, in German Offenlegungsschriften Nos. 2,035,731 and 2,123,183.

3. Also for preparing solid products, solutions within a viscosity range of 10,000 to 100,000 cP at 25°C of uretdione polyisocyanates, trimerized polyisocyanates, urethane-, biuret- or allophanate- polyisocyanates in liquid phosgenation products of aniline formaldehyde condensates.

Although sulphonation can be carried out at lower viscositites, substantial quantities of solid crystalline sulphonation products are then frequently deposited. Phosgenation products which have a viscosity of 100 cP to 2000 cP at 25°C are quite particularly suitable.

Commerical distillation residues such as are obtained from the distillation of commercial tolylene diisocyanate mixtures and which contain less than 50% by weight of free tolylene diisocyanate isomers are also eminently suitable for the process of the invention. Distillation residues of this kind can be obtained, for example, by the process described in U.S. Pat. No. 3,215,652. The distillation residues described in U.S. Pat. No. 3,455,836 and their solutions in the phosgenation products of aniline/formaldehyde condensates are also particularly suitable. Distillation residues obtained according to the process of U.S. Pat. application Ser. No. 161,817 filed on July 12, 1971, as well as solutions of such residues in the phosgenation products of aniline/formaldehyde condensates as those described in Belgian Pat. No. 783,257 may also be used in the process of this invention. Other distillation residues as more particularly disclosed below may also be used.

Other liquid aromatic polyisocyanate mixtures suitable for the process according to the invention are the phosgenation products of the condensates of aniline and aldehydes or ketones such as acetaldehyde, propionaldehyde, butyraldehyde, acetone, methyl ethyl ketone, and the like as well as phosgenation products of condensates of anilines which are alkylsubstituted on the nucleus, particularly condensates of toluidines with aldehydes or ketones such as formaldehyde, acetaldehyde, butyraldehyde, acetone, methyl ethyl ketone, and the like, some of which are disclosed in U.S. Pat. No. 2,683,730.

Reaction products of the above mentioned aromatic polyisocyanates with 0.2 to 25 mols percent of polyols are also suitable for the process of the invention, provided that the viscosity of the resulting reaction products does not exceed 10,000 cP at 25°C and that the NCO content of the reaction products is at least 10% by weight. Suitable polyols for the modification of the starting materials are in particular, the known polyether and/or polyester polyols well known in polyurethane chemistry which are in the molecular weight range of 200 to 6000, preferably 300 to 4000, and low molecular weight polyols in the molecular weight region of 62 to 200.

Examples of such low molecular weight polyols are for example, ethylene glycol, propylene glycol, glycerol, trimethylol propane, hexane-1,3,6-triol and the like.

Other suitable starting compounds for the process of the invention are the reaction products of the common organic polyisocyanates known to the art of polyurethane chemistry such as, for example, 2,4-diisocyanatotoluene, 2,6-diisocyanatotoluene, 4,4'-diisocyanatodiphenylmethane, and the like, with 1 to 25 mols percent of the polyols mentioned above, the same restrictions applying to the reaction products as regards their NCO content and viscosity. These starting materials for the process of the invention in all cases comprise mixtures which contain at least two different isocyanates.

When using the phosgenation products of aniline/formaldehyde which contain a particularly low proportion of dinuclear isocyanates and therefore have an undesirably high viscosity, for example, more than 5000 cP, it may be advisable to add 1 to 30% by weight of tolylene diisocyanate or 2,4'-diphenylmethane diisocyanate in the pure or crude commercial form before or after sulphonation in order to lower the viscosity.

The sulphonating agents used may be the substances commonly used for this purpose in the art, in particular sulphur trioxide, oleum, sulphuric acid and chlorosulphonic acid. From about 10 to about 65% by weight based on the weight of polyisocyanate of oleum or sulphur trioxide are preferred for making liquid products while oleum having a sulphur trioxide content of 20 to 70% or sulphur trioxide is preferred for preparing a solid product.

Sulphonation may be carried out either in the presence of solvents or by directly mixing the reactants. The solvents used should be both inert towards isocyanate groups and inert towards the sulphonating agent under the reaction conditions.

The solvents used are preferably halogenated hydrocarbons such as dichloroethane, tetrachloroethane, fluorotrichloromethane, methylene chloride, chlorobenzene, o-dichlorobenzene, nitromethane, and the like. The halogenated hydrocarbons used are preferably those which have a boiling point of between 0° and 140°C. Sulphonation is carried out at temperatuers of between −20° and 200°C, preferably between 20° and 100°C. The polyisocyanate is generally introduced into the reaction vessel first and may be in the form of a solution at a concentration of 20 to 100%, and the sulphonating agent, which may also be dissolved in an inert solvent such as dichloroethane, is then added with stirring, generally over a period of between a few minutes and several hours. The sulphonating agent is preferably mixed with the polyisocyanate mixture at room temperature and the resulting mixture is then heated to a temperature of 60° to 140°C to complete the reaction. Heating may be omitted without any harmful effects if it is expected that the sulphonated product will be stored for any length of time.

The viscosity of the reaction mixture generally increases during sulphonation. In the preparation of liquid sulphonated isocyanates it is therefore, necessary to ensure that the quantity of sulphonating agent used is not too high and it should in no cases exceed 10% of sulphur trioxide, based on the quantity of unsulphonated isocyanate, or an equivalent quantity of oleum, sulphuric acid or chlorosulphonic acid. The quantity of sulphur trioxide used is generally less than 6%. The lower limit is in the region of 0.1% preferably 0.2%. Although the quantity used may well be below this limit, isocyanates which have only been slightly sulphonated are generally of little commercial value. It is particularly preferred to use quantities of from 0.4% to 5% of sulphur trioxide.

According to a particularly preferred embodiment of the process, gaseous sulphur trioxide is used for sulphonation. The reaction may be carried out at room temperature or moderately elevated temperature, for example 35° to 100°C, by passing sulphur trioxide into the liquid polyisocyanate or over its surface either in the presence or absence of solvents. One suitable method consists in passing the sulphur trioxide into the space above the liquid surface at a slight excess pressure, the sulphur trioxide may be mixed with an inert gas such as nitrogen. Mixing is effected simply by vigorously stirring the liquid phase.

According to one particularly advantageous method of carrying out this process, the gasification with sulphur trioxide is carried out at 100° to 200°C, preferably 150°C to 200°C, i.e., at a temperature at which uretdiones are reversibly decomposed. A particular advantage of this method is that sulphonation can be carried out directly after the phosgenation stage, before or after the chlorobenzene normally used for this purpose is distilled off. It is particularly economical, and therefore preferred, to carry out the gasification of the solutions of polyisocyanate mixtures in chlorobenzene while they are still hot, immediately after phosgenation. It has surprisingly been found that sulphonation products prepared using sulphur trioxide by the process according to the invention have a uretdione group content of about 0.1 to 8% independent of the temperature employed for sulphonation. If the sulphonation is carried out using oleum or sulphuric acid, the sulphonation products are in most cases found to contain uretdione groups but particularly urea and biuret groups.

The degree of sulphonation in the product which is obtained in the liquid aggregate state depends, among other factors, on the viscosity of the isocyanate mixture used.

Low viscosity products can easily be sulphonated to a high degree of sulphonation whereas if the initial viscosity is higher than 5000 cP, the amount of sulphur trioxide used for the sulphonation is generally not more than 5%. Isocyanates which have a viscosity below 100 cP are also preferably sulphonated with up to 5% of sulphur trioxide.

Sulphonation is preferably carried out by gasifying the reaction mixture with sulphur trioxide at 50° to 200°C, in particular 80° to 180°C when preparing solid products. This is achieved e.g. by passing a stream of nitrogen through a 65% oleum and conducting the gas mixture into or over the reaction mixture. The reaction with sulphur trioxide is practically instantaneous. Inert solvents may be included if means are provided for removing them at the end of the reaction.

If the degree of sulphonation is high, e.g., with more than 15% of sulphur trioxide, part of the solvent (e.g., 10 to 50%, based on the sulphonated isocyanate) may be left in the product, provided that the product remains a resinous solid in spite of its solvent content. The use of solvents has the advantage that the sulphonation of even highly viscous products can be carried out at room temperature.

Oleum with a sulphur trioxide-content of 20 to 70% may also be used for sulphonation, particularly if only low degrees of sulphonation of not more than 12% by weight of sulphonic acid groups are desired. The use of oleum has, however the disadvantage compared with the use of pure sulphur trioxide that it causes a reduction in the isocyanate content owing to the side reaction between sulphuric acid and isocyanates. Sulphuric acid and chlorosulphonic acid are less suitable for preparing solid non-crystalline products.

The aromatic isocyanatosulphonic acids obtained by the process according to the invention may be partly or completely neutralized to the corresponding isocyanatosulphonates after preparation. These isocyanatosulphonates may be liquid compounds with viscosities in the range of 100 to 80,000 cP at 25°C. Suitable neutralizing agents are organic or inorganic bases such as trimethylamine, triethylamine, tributylamine, dimethylaniline, urotropine, sodium bicarbonate, sodium hydroxide, calcium carbonate, magnesium carbonate, calcium hydroxide, magnesium hydroxide, calcium oxide, magnesium oxide, zinc oxide or sodium phosphate. Inorganic neutralizing agents which do not have a strong basic reaction, such as calcium carbonate, magnesium carbonate, dolomite, chalk or sodium phosphate, may also be used in large excess as fillers. The hydrophilic character and reactivity of the products according to the invention is increased by conversion of the sulphonic acid groups to corresponding sulphonate groups.

The neutralization of the isocyanate sulphonic acids first formed is often accompanied by an increase in viscosity. It is only when tertiary amines are used that a fall in viscosity can be observed. Furthermore, both the hydrophilic character and the reactivity of the products increase considerably. In some cases, this results in a reduction in stability in storage.

If neutralization is required, it is therefore advisable in these cases to carry it out only shortly before the product is to be used. Furthermore, it has been found advantageous to carry out only a partial neutralization, e.g., of 5 to 40% based on the theoretical quantity of $SO_3H$-groups (calculated from the sulphur content). If amines or strong alkalis are used for neutralization, a degree of neutralization of 5 to 20% is preferred. It is only when neutral salts or weak bases which have the character of fillers are used as neutralizing agents, such as magnesium carbonate, calcium carbonate, barium carbonate, zinc carbonate, calcium acetate, calcium oxalate, magnesium oxide, zinc oxide, iron hydroxide or cement that the neutralizing agent may, without risk, be used in excess.

Neutralization is preferably carried out by adding the above mentioned solid neutralizing agents, which have the character of a filler, after the product has been cooled in order to facilitate pulverization of the product. If spray pulverization is employed, the already pulverized product may be mixed with neutralizing fillers.

If inorganic neutralizing agents are used, care should be taken to insure that the water liberated in the neutralization reaction reacts with the isocyanate groups, in particular to form urea groups. If it is desired to avoid the resulting reduction in isocyanate-content, it is advisable to use tertiary amines as neutralizing agents, e.g., triethylamine or pyridine.

The sulphur content of the products of the process is in most cases lower than the quantity calculated from the quantity of sulphur trioxide put into the reaction because, in the presence of diphenylmethane derivatives, part of the sulphur is lost by the evolution of sulphur dioxide. Because of the relatively high temperature, preferably 80° to 180°C at which the process according to the invention is carried out, the products of the process contain, besides sulphonic acid groups, varying proportions of by-products, in particular of the kind formed by the reaction between sulphonic acid groups and isocyanate groups at elevated temperatures. The solid products obtained by employing the process according to the invention, however, are invariably soluble or at least dispersible, in aqueous alkalis at 60° to 100°C because of their free sulphonic acid groups or, if the sulphonic acid groups have already been partly or completely neutralized, the products are soluble or at least dispersible in water.

The preferred solid products according to the invention are characterized by a. a softening point according to DIN 53 460 of at least 35°C (under a load of 1 kp),
b. an isocyanate-content of 3 to 20 and preferably 3 to 8 percent by weight and
c. a sulphur content of 2.2 to 10 and preferably 2.6 to 6.5 percent by weight.

The liquid polyisocyanates containing sulphonic acid and/or sulphonate groups obtainable by the process of the invention are characterized by a. an NCO content of 10 to 42 percent by weight, preferably 18 to 35 percent by weight;
b. a sulphonic acid and/or sulphonate group content of 0.1 to 8 percent by weight, preferably 0.2 to 6 percent by weight;
c. a uretdione and/or urea or biuret and/or urethane or allophanate group content determined with IR spectroscope of in each case up to about 10 percent by weight; and
d. a viscosity of 100 to 80,000 cP at 25°C.

The groups mentioned under (c) may be formed by side reactions in the course of sulphonation. Urethane and/or allophanate groups are, of course, also present in the products of the process if polyol modified polyisocyanates are used as starting materials.

The polyisocyanate sulphonic acids obtained by the process according to the invention which are liquid and have an NCO content of between 10 and 42% preferably 18 to 35% were previously unknown. They are in many ways excellent for the production of foam resins and compact synthetic resins. They can easily be processed by the usual techniques such as casting processes and by means of the usual conveyor and dosing systems.

The sulphur content of the products of the process can be determined by elementary analysis in known manner. The isocyanate-content can be determined by the conventional method with dibutylamine. When determining the isocyanatecontent, however, it is necessary to take into account the consumption of dibutylamine by the neutralization reaction with free sulphonic acid groups, which in turn can be determined quantitatively by potentiometric titration.

In preparing solid products, it is preferred to operate within two restricted ranges because resins or resinous powders with exceptionally advantageous properties are then obtained:

1. Sulphonation of isocyanate mixtures which have a viscosity of 50 to 10,000 cP (25°C) with 12 to 32 percent by weight of sulphur trioxide.
2. Sulphonation of isocyanate mixtures which have a viscosity of between about 15,000 and 100,000 cP (25°C) with 6 to 20 percent by weight of sulphur trioxide.

As already mentioned above, particularly preferred products are pulverulent sulphonated polyisocyanates with an isocyanate-content of 3 to 8% by weight and a sulphur content, introduced by means of sulphonating agents, of 2.6 to 6.5% by weight, and a softening range above 35°C.

Solid products of this kind are obtained when liquid isocyanate mixtures which have an average functionality of more than 2.2, an isocyanate-content of 18 to 35% by weight and a viscosity of 400 to 10,000 cP at 25°C are mixed with 12 to 20% by weight of sulphur trioxide or an equivalent quantity of high-percentage oleum with a sulphur trioxide content of 20 to 70% in such a way that the temperature at the end of the mixing process is between 80° and 180°C, and the brittle-solid resin formed after cooling is pulverized or sprayed hot, the spray mist being obtained in the form of a powder when cold, the product being optionally completely or partly neutralized before or after cooling.

The terms "sulphonated polyisocyanates" and "aromatic polyisocyanates which contain sulphonic acid groups and/or sulphonate groups" are, of course, taken to include also the equilibrium mixtures which are formed in known manner by the reaction of sulphonic acid groups with isocyanate groups and which comprise in particular the adducts which contain mixed anhydride groups and their secondary products. The only essential requirement for the purpose of this invention is that the products should behave like isocyanate sulphonic acids, i.e., they should both enter into typical isocyanate reactions (reaction with Zerewitinoff-active secondary amines or alcohols, evolution of carbon dioxide on addition of water) and behave like acids (pH below 2 in water, capable of being neutralized with bases). A feature which is of major importance for their practical application and characteristic of them is the ease with which they can be emulsified without emulsifying agent in alkaline aqueous media, e.g., in 1 to 10% sodium hydroxide or sodium silicate solution at 60° to 100°C.

The solid and preferably pulverulent products obtainable by the process according to the invention are new and versatile in their application. They are readily soluble or dispersible in water or aqueous alkalis even when they are still in the form of free sulphonic acids but especially in the form of their salts. Because of their hydrophilic character they are easily hardened by atmospheric moisture. This hardening reaction is accompanied by chain-lengthening or cross-linking resulting in the formation of polyureas. Because of these properties, the products are suitable for use as emulsifiers or wetting agents, for the production of ion exchangers, as hydraulic binders, as thickeners in aqueous systems, as surface-coating agents and as cross-linking agents for vinyl polymers, polyurethanes, polyureas, and polyamides.

As highly sulphonated isocyanates they are almost completely non-toxic and the substances obtained when the polymers formed from the products undergo degradation are also non-toxic.

In contrast to corresponding organic polyisocyanates which are not sulphonated, the liquid products according to the invention have excellent compatibility both with hydrophobic and with hydrophilic reactants and particularly with polyethylene oxide polyethers, ionomeric glycols and amine salts of various kinds, water and aqueous salt solutions. The polyisocyanates according to the invention are therefore particularly valuable for the production of hydrophilic foam resins by the isocyanate polyaddition process, particularly for the production of ionomeric foams which may be used, for example, as ion exchangers and agricultural foams.

The invention is further illustrated but it is not intended that it be limited by the following examples wherein all parts and percentages are by weight unless otherwise indicated.

The following starting materials are employed in Examples 1 through 17:

I Reaction product of about 1 mol of tripropylene glycol and about 5 mols of 4,4'-diphenylmethane diisocyanate (23 percent NCO).

II Sufficient diisocyanatodiphenylmethane is distilled from crude phosgenation product of an aniline/formaldehyde condensate to leave a distillation residue having a viscosity of about 100 cP at 25°C (dinuclear portion: 59.7 percent; trinuclear portion: 21.3 percent; portion of higher nuclear polyisocyanates: 19.0 percent).

III Similarly prepared polyisocyanates with a viscosity of about 200 cP at 25°C (dinuclear portion: 44.3 percent; trinuclear portion: 23.5 percent; portion of higher nuclear polyisocyanates: 32.2 percent).

IV Similarly prepared polyisocyanates with a viscosity of about 400 cP at 25°C (dinuclear portion: 45.1 percent; trinuclear portion: 22.3 percent; portion of higher nuclear polyisocyanates: 32.6 percent).

V Similarly prepared polyisocyanate with a viscosity of about 500 cP at 25°C (dinuclear portion: 40.6 percent; trinuclear portion: 27.2 percent; portion of higher nuclear polyisocyanates: 32.2 percent).

VI Similarly prepared polyisocyanate with a viscosity of about 1700 cP at 25°C (dinuclear portion: 40.3 percent; trinuclear portion: 34.0 percent; portion of higher nuclear polyisocyanates: 25.7 percent).

VII 20 percent solution in a crude phosgenation product of an aniline/formaldehyde condensate of a distillation residue obtained from the distillation of commercial tolylene diisocyanate: Viscosity at 25°C: 1260 cP; NCO content: 29.3 percent.

VIII 40 percent solution of the above mentioned distillation residue in the crude phosgenation product of an aniline/formaldehyde condensate. Viscosity at 25°C: 2970 cP; NCO content: 29.6 percent.

GENERAL METHOD OF PREPARATION USED IN EXAMPLE 1 to 16:

The aromatic polyisocyanate is introduced into the reaction vessel and the sulphonating agent is added dropwise at the given temperature. The reaction mixture is stirred, filtered if necessary, and any solvent present distilled off at reduced pressure if necessary.

| Example | Isocyanate, parts | Dichloroethane, parts | 65% Oleum parts | SO₃ parts | 33.3% SO₃ in dichloroethane, parts | Temp. °C | Stirring time °C | End product S content % | NCO content % | Viscosity cP/25°C |
|---|---|---|---|---|---|---|---|---|---|---|
| 1 | 870 I | — | 20 | — | — | 52–76 | — | 0.2 | 21.1 | thin liquid |
| 2 | 500 I | — | — | 20 | — | 23–68 | 3 hrs. 68–25 | | | thick liquid |
| 3 | 500 IV | 250 | — | — | 71 | 22–31 | 45 min. 70 | 1.5 | | " |
| 4 | 2000 IV | 1000 | — | — | 286 | 22–33 | 30 min. 70 | 1.5 | 30.5 | 24,300 |
| 5 | 2000 IV | 400 | — | — | 143 | 22–28 | 30 min. 70 | 0.8 | 30.7 | 1,400 |
| 6 | 500 I | 250 | — | — | 73 | 22–31 | 30 min. 70 | | 25 | thick liquid |
| 7 | 2000 I | 1000 | — | — | 144.5 | 22–29 | 1 hr. 65–70 | 0.75 | 25 | 45,000 |
| 8 | 2000 I | 1000 | — | — | 120 | 22–26 | 1 hr. 68–70 | 0.8 | 25 | 6,000 |
| 9 | 200 VII | 100 | — | — | 13.5 | 22–27 | 30 min. 70 | 0.7 | 29 | about 20,000 |
| 10 | 200 VII | 100 | — | — | 21.5 | 22–28 | 30 min. 70 | 1.3 | 29 | about 50,000 |
| 11 | 200 VIII | 100 | — | — | 13.5 | 23–27 | 30 min. 70 | 0.8 | 29 | about 50,000 |
| 12 | 1000 II | 200 | — | — | 71.5 | 24–28 | 30 min. 70 | 0.67 | 31.4 | 197 |
| 13 | 1000 III | 200 | — | — | 71.5 | 25–29 | " | 0.62 | 31.4 | 480 |
| 14 | 1000 IV | 200 | — | — | 71.5 | 24–28 | " | 0.70 | 31 | 800 |
| 15 | 1000 V | 200 | — | — | 71.5 | 24–29 | " | 0.72 | 30.5 | 1,071 |
| 16 | 1000 VI | 200 | — | — | 71.5 | 23–28 | " | 0.69 | 30.8 | 3,240 |

EXAMPLE 17

Sulphonation of IV with gaseous sulphur trioxide.

About 500 g of IV are heated to about 170°–175°C in a 2 liter three-necked flask with Claisen attachment equipped with a tube for passing gas over the surface of the reactants, a mechanical stirrer, an internal thermometer and a drying tube. 44 V 40 is reacted with about 13.2 g of SO₃ obtained by heating 65% oleum to about 120°C, the SO₃ tube being held about 2 to 4 centimeters above the surface of the liquid for about 2 hours while vigorously stirring the IV. The product obtained is a sulphonated IV having the following properties:

| Sulphur content %: | 0.69, |
| NCO content %: | 29, |
| Viscosity, cP/25°C: | 6075. |

EXAMPLE 18

1000 g of a crude phosgenation product of an aniline formaldehyde condensate from which sufficient dinuclear constituent was distilled off to result in a distillation residue with a viscosity of 400 cP were gasified with sulphur trioxide at 100° to 110°C. 98 g of sulphur trioxide (9.8% based on the isocyanate) were taken up in 18 hours. The product was poured out at 140°C and solidified when cold to a brittle resin. The theoretical sulphonic acid group content, calculated from the sulphur content of 3.3 is 8.2%. The resin can be crushed to a powder in a mortar.

EXAMPLE 19

A phosgenation product similar to that of Example 18 which had a viscosity of 2000 was sulphonated with 92 g of sulphur trioxide at 100° to 140°C. The highly viscous reaction mixture solidified to a brittle resin at room temperature. The theoretical sulphonic acid group content calculated from the sulphur content of 2.6% is 6.5%.

EXAMPLE 20

100 g of a 25% solution of a distillation residue from the distillation of commercial tolylene diisocyanate in the crude phosgenation product of an aniline formaldehyde condensate (viscosity at 25°C: 15,000 cP; isocyanate-content 28 percent by weight) were gasified with 12 g of sulphur trioxide while the temperature gradually rose from 40°C to 160°C. The highly viscous mass was poured out at 150°C and solidified to form a springy-hard resin which could be pulverized at room temperature. The sulphonic acid group content was calculated from the sulphur content of 3.3% to be 8.2. Pulverization is facilitated by carrying it out in the presence of 40 g of calcium carbonate.

EXAMPLE 21

The procedure was the same as in Example 20 but it was carried out with the addition of 200 g of tetrachloroethane and 26 g of sulphur trioxide (26%). The product was passed through an evaporator screw and ground up.

EXAMPLE 22

The procedure was the same as that described in Example 20 but using only 6.5 g (6.5%) of sulphur trioxide. An amorphous, hard resin was again obtained in this experiment.

EXAMPLE 23

When 130 g of sulphur trioxide were used instead of 98 g in Example 18, the temperature had to be raised to 150°C during the sulphonation process. A resin which could very easily be pulverized was then obtained. When on the other hand, only 40 g of sulphur trioxide were added, the resulting resin could not be pulverized.

EXAMPLE 24

The same procedure was used in Example 18 but 125 g of sulphur trioxide were used (12.5% based on the isocyanate). 32 g (0.156 mol = 10% of the theory) of N,N-dibutyl aniline were then stirred in dropwise. This resulted in a slight decrease in viscosity. The product was poured out at 140°C and solidified to a brittle resin when cold. The sulphur content was 3.9%.

EXAMPLE 25

The product produced according to Example 18 could be pulverized considerably more easily if, after the addition of sulphur trioxide, 56 g of calcium oxide were stirred into the mixture in a finely powdered form. This was accompanied by an increase in viscosity.

EXAMPLE 26

900 g of a crude phosgenation product of an aniline formaldehyde condensate, from which dinuclear constituents were distilled off until the distillation residue had a viscosity of 100 cP, and 100 g of tolylene diisocyanate (isomeric mixture 65:35) were gasified with sulphur trioxide, first at room temperature and then with gradual heating to 120°C. A total of 150 of sulphur trioxide was taken up in 10 hours. The product was poured out while still hot and solidified to a brittle, glassy mass when cold. Sulphur content 4.6%.

EXAMPLE 27

50 g of the resin obtained in Example 26 were finely powdered with the addition of 10 g of calcium oxide. The mixture was mixed to a paste with 30 g of cyclohexanone at 150°C and this mixture was then rapidly and vigorously mixed with 40 g of saturated soda solution at 20°C, a thick, milky white liquid emulsion (W/O-type) being obtained which hardened to a cross-linked, diphasic synthetic resin within 2 minutes.

EXAMPLE 28

500 g of a crude phosgenation product of an aniline formaldehyde condensate from which the required quantity of dinuclear constituent had been distilled off to result in a distillation residue with a viscosity of 170 cP were diluted with 250 g of 1,2-dichloroethane. A solution of 72 g of sulphur trioxide in 144 g of dichloroethane was added dropwise at room temperature over a period of 2 hours, the temperature rising to 37°C. The product was filtered from minor quantities (about 5 g) of precipitate and free from solvent by heating to 60°C in a vacuum. A hard, brittle resin was obtained on cooling. A sample of the resin in a small quantity of dichloroethane could easily be emulsified in a 2%-solution of sodium hydroxide at 80°C.

A few drops of triethylamine were added to another sample of the resin in a small quantity of dichloroethane, and the resin could then easily be emulsified in hot water by shaking.

EXAMPLE 29

The procedure was the same as in Example 28 but 138g of sulphur trioxide (27.6% based on the isocyanate) in 530 g of dichloroethane were used. The product was a springy-hard resin at room temperature even when it still contained about 200 g of dichloroethane.

EXAMPLE 30

A solution of 30 g of sulphur trioxide in 100 g of dichloroethane was added dropwise at 60°C to 500 g of a crude phosgenation product of an aniline formaldehyde condensate, from which the required quantity of dinuclear constituents had been distilled off to result in a distillation residue with a viscosity of 80,000 cP and most of the solvent was then distilled off under vacuum at 90° to 100°C. The product solidified to a hard resin on cooling. A sample of the resin could be emulsified in a 2%-solution of sodium hydroxide at 90°C. A solution of the product in dichloroethane or cyclohexanone was suitable for impregnating or coating concrete.

Although mixtures of the distillation residues of diisocyanato-toluene and diisocyanatodiphenyl methane as described in U.S. Pat. No. 3,455,836 may be used, these products contain such a high amount of the distillation residue that they do not have satisfactory solubility. Therefore, it is preferred that a sediment-free solution of the diisocyanatotoluene distillation residues have a higher concentration of ortho-diamine phosgenation products which correspond to a concentration of less than 15% by weight of the distillation residue.

Thus it is preferred to employ a polyisocyanate mixture which comprises:

a. from 2 to 60% by weight of a distillation residue obtained from a large-scale distillation of crude isocyanatotoluene isomer mixtures, having a carbodiimide group content of less than 1.4% by weight, a content of, phosgenation products of 2,3- and 3,4-diaminotoluene, or secondary products thereof, corresponding to a content of more than 2% by weight of o-diamine in the amine mixture used for phosgenation, an NCO-group content of from 15 to 32% by weight, and a monomeric diisocyanatotoluene content of less than 15% by weight, and b. from 40 to 98% by weight of a polyphenyl-polymethylene-polyisocyanate mixture comprising from 50 to 100% by weight of binuclear diisocyanato diphenylmethane isomers, obtained by phosgenating aniline/formaldehyde condensates.

The distillation residues employed in the mixtures according to the invention may be formed by the distillative working up of the phosgenation products of a crude commercial diaminotoluene isomer mixture. The diaminotoluene isomer mixtures used are those obtained by dinitrating toluene, followed by reduction as known per se. Solubility in 4,4'-diisocyanatodiphenyl methane or its isomers and homologues is governed by different factors:

1. The free 2,4- and 2,6-diisocyanatotoluene content of the distillation residues should be less than 15% by weight, preferably less than 10% by weight.
2. The carbodiimide group content (—N=C=N—), identifiable by infra-red spectroscopy, should not exceed 1.4% by weight.
3. The average molecular weight of the distillation residue must be below 1000 for a free diisocyanate content of 15% by weight.

Specifically one may prepare the preferred mixture of distillation residues to be used according to the invention as follows:

4 kg of a distillation residue, resulting from the distillation of high-grade commercial diisocyanatotoluene, having an NCO-group content of 24% by weight, a carbodiimide group content of 1.1% by weight, a free diisocyanatotoluene content of 12% by weight, a content of o-diamine phosgenation products, or secondary products thereof, corresponding to an o-diamine content of 4% by weight in the original amine mixture, are heated to 130°C. The low-viscosity melt thus obtained is intensively stirred with 6 kg of 4,4'-diisocyanatodiphenyl methane heated to 100°C. A polyisocyanate mixture having an NCO-content of 28.6% by weight and a viscosity of 1370 cP (at 25°C) is obtained after cooling. This polyisocyanate mixture is still free from sediment after 5 months.

Corresponding mixtures of 4,4'-diphenyl methane diisocyanate with the same distillation residue have viscosities of 433 cP (25°C) for a distillation residue content of 35% by weight, and a viscosity of 31,000 cP (25°C) for a distillation residue content of 50% by weight.

Although the invention is described in considerable detail in the foregoing it is to be understood that such detail is presented solely for purposes of illustration and that many variations and substitutions may be made therein by one skilled in the art without departing from the spirit and scope of the invention.

What is claimed is:

1. Liquid aromatic polyisocyanates, which contain sulphonic acid or sulphonate groups, prepared by a process comprising reacting at a temperature of from about −20°C to about 200°C:

A. a liquid multicomponent mixture of aromatic polyisocyanate having an NCO content of from about 18% to about 35% by weight, and a viscosity of from about 50 to about 10,000 cP at 25°C, said liquid multicomponent mixture selected from the group consisting of:

i. phosgenation products of the condensates of (a) aniline or alkyl groups substituted anilines and (b) aldehydes or ketones;

ii. distillation residues obtained from the distillation of crude tolylene diisocyanate mixtures and which residues contain less than about 50% by weight of free tolylene diisocyanate isomers;

iii. a reaction product of (i) or (ii) and 0.2 to 25 mol percent of an organic polyol;

iv. a mixture of (i) with from 1 to 30% by weight of tolylene diisocyanate or 2,4'-diphenylmethane diisocyanate; and v. mixtures thereof; and B. from about 0.1 to about 10% by weight, based on the weight of said liquid multicomponent mixture of sulphur trioxide or an equivalent quantity of oleum, sulphuric acid, or chlorosulphonic acid.

2. The polyisocyanate of claim 1, wherein the sulphonating reaction is carried out in an inert solvent.

3. The polyisocyanate of claim 1, wherein the sulphonated reaction product is partially or completely neutralized with a basic compound.

4. The polyisocyanate of claim 1 wherein the liquid multicomponent mixture of aromatic polyisocyanates used is a phosgenation product of aniline/formaldehyde condensates which contains 20 to 80% by weight of dinuclear diisocyanates, 8 to 70% by weight of trinuclear triisocyanates, 1 to 20% by weight of tetranuclear tetraisocyanates and 1 to 40% by weight of higher nuclear polyisocyanates.

* * * * *